US009125689B2

(12) United States Patent
Mielekamp (10) Patent No.: US 9,125,689 B2
(45) Date of Patent: Sep. 8, 2015

(54) CLIPPING-PLANE-BASED ABLATION TREATMENT PLANNING (75) Inventor: Pieter Maria Mielekamp, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 390 days.

(21) Appl. No.: 13/514,075

(22) PCT Filed: Nov. 30, 2010

(86) PCT No.: PCT/IB2010/055491
§ 371 (c)(1),
(2), (4) Date: Jun. 6, 2012

(87) PCT Pub. No.: WO2011/070476
PCT Pub. Date: Jun. 16, 2011

(65) Prior Publication Data
US 2012/0237105 A1 Sep. 20, 2012

(30) Foreign Application Priority Data

Dec. 8, 2009 (EP) .................................... 09178296

(51) Int. Cl.
*G06K 9/00* (2006.01)
*A61B 19/00* (2006.01)
(Continued)

(52) U.S. Cl.
CPC ................ *A61B 19/50* (2013.01); *A61B 18/02* (2013.01); *A61B 19/5212* (2013.01); *A61B 2018/0293* (2013.01); *A61B 2019/504* (2013.01); *A61B 2019/507* (2013.01); *A61B 2019/524* (2013.01);
(Continued)

(58) Field of Classification Search
None
See application file for complete search history.

(56) References Cited

U.S. PATENT DOCUMENTS 6,241,725 B1 * 6/2001 Cosman .......................... 606/41
6,505,065 B1 * 1/2003 Yanof et al. .................... 600/427
(Continued)

FOREIGN PATENT DOCUMENTS

JP 03224547 A * 10/1991 ............... A61B 6/03
JP 07255716 A * 10/1995 ............... A61B 6/03
(Continued)

OTHER PUBLICATIONS

Samset et al., "Intra-Operative Visualisation of 3D Temperature Maps and 3D Navigation During Tissue Cryoablation", Computerized Medical Imaging and Graphics, 2005; 29(6):499-.
(Continued)

*Primary Examiner* — Wenpeng Chen (57) ABSTRACT

Ablation treatment planning comprises: acquiring a three-dimensional (3D) image data set of a region of interest; introducing 3D model data of an ablation volume into the 3D image data set; and drawing, as a 2D image, what remains of a cross sectional multiplanar reformatting (MPR) slice of the region of interest and the ablation volume within an MPR plane by virtue of using the MPR plane as a clipping plane. The introduction is doable by tagging image pixels using a stencil buffer and possibly by culling specific inside areas and/or outside areas of the ablation volume. An ablation volume, for, e.g., receiving a cryoablation needle to eliminate tumor tissue and having any arbitrary shape, may be visualized within a 3D image space by drawing 2D images in any desired MPR plane such that also oblique orientations of the ablation volume can be represented. Subsequently, an ablation needle may be guided to a location and in an orientation as previously planned.

21 Claims, 6 Drawing Sheets (51) Int. Cl.
*G06T 7/00* (2006.01)
*G06T 19/00* (2011.01)
*A61B 18/02* (2006.01)

(52) U.S. Cl.
CPC ....... *A61B 2019/5289* (2013.01); *G06T 7/0012* (2013.01); *G06T 19/00* (2013.01)

(56) References Cited

U.S. PATENT DOCUMENTS

| | | | |
|---|---|---|---|
| 6,529,766 B1* | 3/2003 | Guendel | 600/427 |
| 6,575,969 B1* | 6/2003 | Rittman et al. | 606/41 |
| 6,970,585 B1* | 11/2005 | Dafni et al. | 382/131 |
| 7,402,161 B2 | 7/2008 | Zvuloni et al. | |
| 2004/0085310 A1* | 5/2004 | Snuffer | 345/419 |
| 2004/0130552 A1* | 7/2004 | Duluk et al. | 345/506 |
| 2005/0033160 A1* | 2/2005 | Yamagata et al. | 600/425 |
| 2005/0245826 A1* | 11/2005 | Gervais | 600/443 |
| 2006/0089624 A1 | 4/2006 | Voegele et al. | |
| 2006/0103669 A1* | 5/2006 | Piccuezzu et al. | 345/620 |
| 2006/0109266 A1* | 5/2006 | Itkowitz et al. | 345/419 |
| 2007/0206008 A1* | 9/2007 | Kaufman et al. | 345/424 |
| 2008/0033419 A1* | 2/2008 | Nields et al. | 606/27 |
| 2008/0049991 A1* | 2/2008 | Gering | 382/128 |
| 2008/0094412 A1* | 4/2008 | Jiao et al. | 345/621 |
| 2008/0270095 A1* | 10/2008 | Lombaert et al. | 703/11 |
| 2009/0082660 A1* | 3/2009 | Rahn et al. | 600/411 |
| 2009/0118609 A1* | 5/2009 | Rahn | 600/411 |
| 2009/0118613 A1* | 5/2009 | Krugman et al. | 600/431 |
| 2009/0124896 A1* | 5/2009 | Haras | 600/427 |
| 2009/0129652 A1* | 5/2009 | Zwirn et al. | 382/131 |
| 2009/0142740 A1 | 6/2009 | Liang et al. | |
| 2009/0148009 A1* | 6/2009 | Mielekamp et al. | 382/128 |
| 2009/0184960 A1* | 7/2009 | Carr et al. | 345/422 |
| 2009/0196480 A1* | 8/2009 | Nields et al. | 382/132 |
| 2009/0278846 A1* | 11/2009 | Gulsun et al. | 345/423 |
| 2010/0049031 A1* | 2/2010 | Fruland et al. | 600/411 |
| 2010/0063496 A1* | 3/2010 | Trovato et al. | 606/34 |
| 2010/0305439 A1* | 12/2010 | Shai et al. | 600/439 |
| 2010/0316268 A1* | 12/2010 | Liang et al. | 382/128 |
| 2011/0137158 A1* | 6/2011 | Sumanaweera et al. | 600/427 |
| 2012/0189998 A1* | 7/2012 | Kruecker et al. | 434/272 |

FOREIGN PATENT DOCUMENTS

| | | | |
|---|---|---|---|
| JP | 2005080989 A | 3/2005 | |
| JP | 2006116318 | 5/2006 | |
| WO | WO0007501 | 2/2000 | |
| WO | WO0209571 | 2/2002 | |
| WO | WO2005112775 | 12/2005 | |
| WO | WO2007113703 | 10/2007 | |
| WO | WO2008090484 | 7/2008 | |
| WO | WO 2008090484 A2 * | 7/2008 | A61B 19/00 |

OTHER PUBLICATIONS

Ferguson, "Intersections of Ellipsoids and Planes of Arbitrary Orientation and Position", Mathematical Geology, 1979; 11(3):329-336.

* cited by examiner

CLIPPING-PLANE-BASED ABLATION TREATMENT PLANNING

FIELD OF THE INVENTION

The present invention relates to an ablation treatment planning method and to an ablation treatment planning and needle guiding method. Furthermore, the present invention relates to devices for performing such methods, to a computer program adapted for controlling such methods when executed on a computer and a computer-readable medium having stored thereon such computer program.

BACKGROUND OF THE INVENTION

In order to treat cancer, it may be necessary to remove or destroy tumourous tissue in a body of a patient. Due to advances in imaging technology and the availability of highly controllable medical devices, ablation technology is becoming a viable treatment option for a variety of non-resectable tumours.

Currently, three ablation methods are commonly used:

RFA (radio frequency ablation) is the most commonly used ablation method that kills tumourous tissue by converting radio frequency energy into heat. RFA devices typically come with diameters of 1.2 to 1.6 mm and may produce ablation zones with a diameter of 1.5-7 cm.

Another widely available ablation therapy method is cryoablation, where instead of heating the tissue, freezing is used to cause necrosis of tissue. In this method, cell death is due to rapid freezing of intercellular water. To freeze the tumourous tissue, special needles may be placed percutaneous, i.e. through the skin, into the tumour. Argon gas is delivered through the needle thereby producing an iced ablation volume of predictable size and shape. Cryoablation devices typically come with diameters of 1.2-8 mm and may produce ablation zones having a diameter of 4-5 cm.

Microwave ablation is an upcoming thermal ablation technology in which tissue may be heated using microwaves. Microwave ablation probes typically come with diameters of 1.2-5.7 mm and produce ablation zones having a diameter of 1.7-6 cm.

Figure 1:
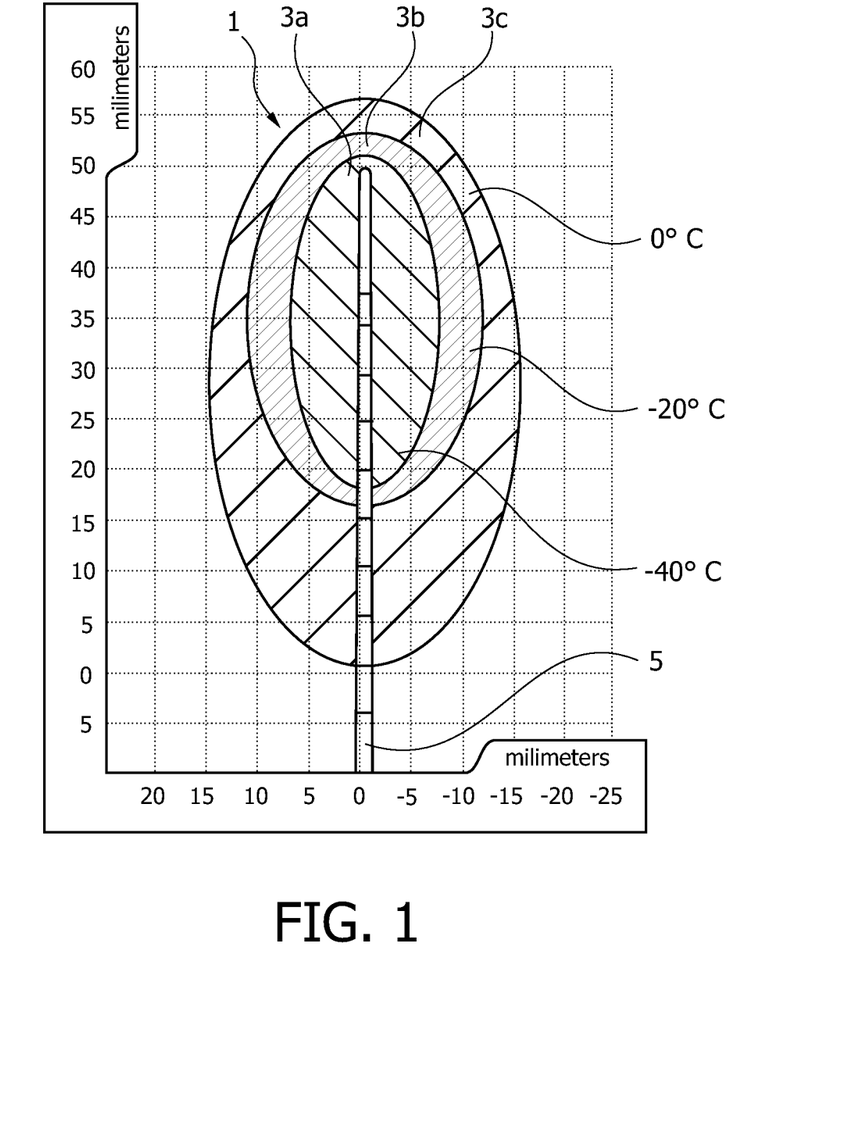
FIG. 1 shows regions of an ablation volume created by a cryoablation needle.

The predicted ablation volume within which a specific ablation device is intended to ablate/kill tumourous tissue, are usually determined and supplied by the device manufacturers. For example, with cryoablation devices, isotherms are generally specified at three different temperatures as shown in FIG. 1. Therein, various volume regions $3a$, $3b$, $3c$ may be defined within an overall ablation volume 1 generated by a cryoablation needle 5 such that the surface of each volume region $3a$, $3b$, $3c$ is defined at a location having a respective temperature such as for example −40°, −20° and 0°. Accordingly, a volume inside an isotherm has a temperature below the temperature value of the isotherm. Thus, the 0°-isotherm defines the overall ablation volume 1 within which tissue is iced during cryoablation. As the ablation needle 5 forms a symmetry axis during a cooling process, each of the ablation regions $3a$, $3b$, $3c$ as well as the overall ablation volume 1 corresponding to the 0° C.-ablation region $3c$ may have an ellipsoid or spheroid shape. For example, the spheroid enclosing the highest temperature volume region $3c$ may have main axis having dimensions of 32 mm×56 mm whereas the inner volume region $3a$ enclosed by the −40° C.-isotherm may have dimensions of 14.5×34 mm. An ice front may extend about 6 mm in front of a needle tip.

During an ablation procedure, a patient is usually positioned in a CT or MRI scanner and one or more ablation needles are inserted into the tumourous tissue under guidance of real-time CT fluoroscopy or ultrasound. The procedure is most often performed by an interventional radiologist in a radiology department of a hospital.

Therein, some of the challenges for achieving of successful necrosis typically are:

a treatment of intermediate and large tumours having for example dimensions larger than the typical dimensions of an ablation volume of an ablation needle;

a precise and reproducible ablation needle placement, i.e. an insertion of the ablation needle into the patient's body towards a correct location within the tumourous tissue such that a location and an orientation of the ablation needle is chosen such that during an ablation process all of the tumourous tissue is destroyed.

A preferred method of creating a large and/or complex ablation volume is to use a plurality of ablation needles with multiple overlapping ablation volumes. Conventionally, such overlapping ablation volumes may be mostly created in the mind of an interventional radiologist without visual feedback. Due to the fact that, for the example of cryoablation, ablation isotherms are usually asymmetric sized, i.e. may have an ellipsoid shape, depending on a needle insertion direction, an effected area may be determined by both an ablation needle target location and an ablation needle insertion direction/orientation. Thus, it may be clear that precise control of an effected ablation volume may be difficult without precise and reliable assistance by a user such as a surgeon or a radiologist, especially at oblique insertion angles of the ablation needle.

SUMMARY OF THE INVENTION

Accordingly, there may be a need for an ablation treatment planning method as well as for an ablation treatment planning and guiding method allowing to reliably plan an ablation volume within a region of interest comprising for example tumourous tissue within a patient and, optionally, subsequently guiding an ablation needle in order to locate and orient the needle such that the ablation volume is ablated during an ablation procedure. Particularly, it may be desired to provide such ablation treatment planning method allowing ablation needle delivery at oblique angles and allowing viewing of the ablation volume coverage at arbitrary plane orientations. Furthermore, there may be a need for an ablation treatment planning device and an ablation treatment planning and guiding device adapted to perform or control such methods, a computer program element adapted for controlling or performing such methods when executed on a computer and a computer-readable medium comprising such computer program element stored thereon.

These needs may be met by the subject matter disclosed herein, including that expressed in the claims.

A success of a percutaneous ablation such as a radio frequency ablation, a cryo-ablation or a microwave ablation, may mainly depend on an accuracy concerning a location and an orientation with which an ablation needle is inserted, enabling to destroy an entire tumour while avoiding damages on other organs and minimizing risks of local reoccurrence.

Recently, a new live 3D needle image planning/guiding procedure has been proposed for example in WO 2007/113703 A2. The needle image planning/guiding system proposed therein has been invented by the applicant of the present invention and is also referred to as XperGuide. This system may allow bringing percutaneous needle interventions back to the angio lab. Such navigational tool may create an overlay of live fluoroscopy imaging and 3D soft tissue imaging that may provide information on needle path and target. XperGuide may be used in a wide range of clinical procedures from biopsies and drainages to ablations. Therein, XperGuide imaging may provide for a live 3D feedback on advancement of a needle for extra guidance and control during interventional procedure. This may allow physicians more freedom in planning and performing needle punctures particularly at oblique angles. Furthermore, optimized patient access for every step of such procedure may be offered. Accordingly, needle guidance procedures may be performed in the angio lab where all the necessary materials may be at hand. Life fluoroscopy may be combined with 3D soft tissue imaging supporting the physician in managing the patient.

In a technique, typically used for soft tissue visualization which is also used by XperGuide, known as multi planar reformatting (MPR), a 2D cross sectional averaged slice with an arbitrary orientation and slice thickness may be interpolated from a three-dimensional volume data set that describes a volume image. Such three-dimensional volume data set may be acquired for example in computed tomography (CT) by calculating a sequence of two-dimensional tomograms that lie in an x-y-plane at predetermined z-coordinates. Alternatively, such three-dimensional volume data may also be reconstructed from a set of 2D images acquired by means of a 3D rotational scan with an X-ray C-arm system. During ablation treatment planning, elliptical cross-sectional areas of the ellipsoid isotherms within a chosen imaging plane may have to be determined in order to support flexible oblique delivery angles of an ablation needle resulting in arbitrarily oriented ablation volumes and arbitrary MPR viewing plane orientation.

In "Intersections of ellipsoids and planes of arbitrary orientation and position", Mathematical Geology, volume 11, no. 3, Jun. 3, 1979, explicit expressions for an axis ratio and orientation of an ellipse, produced by an intersection of a triaxial ellipsoid and a plane which are both arbitrarily oriented is derived. Herein, relationship between central and non-central sections and a problem concerning an intersection probability is discussed. However, the implicit expression of an ellipse produced by the intersection of a triaxial ellipsoid and a plane which may both be arbitrarily oriented may not be trivial to calculate.

Therefore, it is proposed herein to use a more graphics oriented constructive means of tagging an ablation area, thereby allowing to easily plan an ablation volume within a patient's body comprising a region of interest via visualization to a user and, subsequently, allowing to guide an ablation needle to a location and in an orientation such that such ablation volume may be realized.

According to a first aspect of the present invention, an ablation treatment planning method comprising the following steps preferably in the indicated order is proposed: (a) acquiring, e.g. with X-ray imaging using a C-arm X-ray image acquisition device, a 3D image data set of a region of interest; (b) introducing 3D model data of an ablation volume into the 3D image data set; and (c) drawing at least one 2D image comprising a cross sectional MPR slice of the region of interest and the ablation volume within an MPR plane while using the MPR plane as a clipping plane.

According to a second aspect of the present invention, an ablation treatment planning and guiding method is proposed comprising the steps of (i) planning an ablation volume within a region of interest using at least one 2D image drawn in accordance with the method according to the above-mentioned first aspect of the invention wherein a location and an orientation of the ablation volume is predetermined by a planned location and orientation of an ablation needle; and (ii) guiding the ablation needle into the region of interest in accordance with the planned location and orientation.

According to further aspects of the invention, an ablation treatment planning device and an ablation treatment planning and guiding device adapted for performing or controlling the methods according to the above first and second aspect of the invention, respectively, a computer program element adapted for controlling a method according to the above-mentioned first and second aspect of the invention, respectively, and a computer-readable medium having stored thereon a respective computer program element are proposed.

A gist of the present invention may be seen as based on the idea to use a more graphics based approach in order to visualize an ablation volume to be planned within a 3D image of a region of interest such that the ablation area may be visualized in any desired viewing plane orientation. In such graphics based approach, specific image processing procedures such as clipping imaging planes, tagging portions of the 3D model data of the ablation volume through the desired MPR plane into a stencil buffer, blending such tagged portions to a colour buffer, culling an outside or an inside of the ablation volume model, merging of ablation volumes, model transformation for scaling, positioning and/or transforming the 3D model data of the ablation volume in a predetermined direction, etc. may be advantageously used in order to visualize the ablation volume within the region of interest such that a physician may easily plan a subsequent surgical intervention and then guide the ablation needle(s) according to such plan.

In other words, a physician having a 3-dimensional image of a region of interest, e.g. previously acquired with X-ray imaging, may plan an ablation intervention by experimentally inserting simulated ablation volumes having a predictable shape and size into the visualized region of interest within a physiological 3D image at a selectable location and a selectable orientation. The ablation volume should be visualized within the physiological 3D image in a way such that the physician may easily determine whether all tumourous tissue is enclosed within the planned ablation volume. Therein, instead of analytically calculating intersecting areas of a viewing plane with an ellipsoid ablation volume, which may be a difficult task if arbitrarily oriented viewing planes and ablation volume orientations are to be visualized, a graphical approach is used in which the planned ablation volume is visualized within the physiological 3D image using graphics visualization tools.

A basic idea therein may be that, if an MPR image plane is used as a clipping plane while drawing an ablation volume of e.g. spheroid or ellipsoid shape, the 2D cross-sectional ablation areas may show up as portions of the spheroid/ellipsoid that have been cut away and that may show an inside of the spheroid/ellipsoid.

It is to be noted that aspects and embodiments of the present invention are described herein partly with reference to different subject-matters. In particular, some embodiments are described with reference to the method type claims whereas other embodiments are described with respect to device typical claims. However, a person skilled in the art will gather from the above and the following description that, unless other notified, in addition to any combination of features belonging to one type of subject-matter also any combination between features relating to different subject-matters, in particular between features of the device type claims and features of the method type claims, is considered to be disclosed with this application.

BRIEF DESCRIPTION OF THE DRAWINGS

Features and advantages of the present invention will be further described with respect to specific embodiments as shown in the accompanying figures but to which the invention shall not be limited.

Features shown in the drawings are schematic only and not to scale. Throughout the figures, same reference signs refer to same or similar features.

DETAILED DESCRIPTION OF EMBODIMENTS

An ablation treatment planning method according to an embodiment of the present invention will be described with respect to FIGS. 2, 2a, 2b, 2c and 6.

Figure 2:
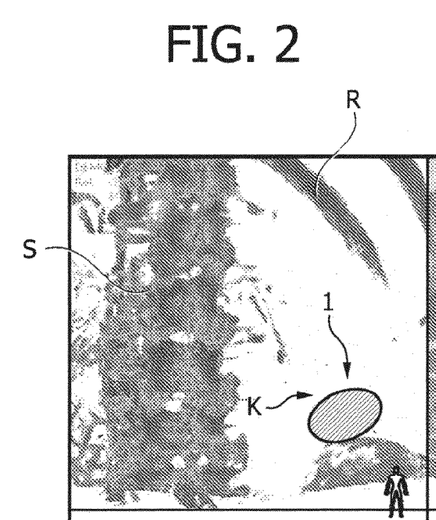
FIGS. 2, 2a, 2b, 2c show presentations of a spheroid ablation volume within a 3D image with an unclipped ablation volume (FIG. 3) and with clipped cross-sectional ablation areas taken at various MPR planes (FIG. 2a,b,c).
Figure 6:
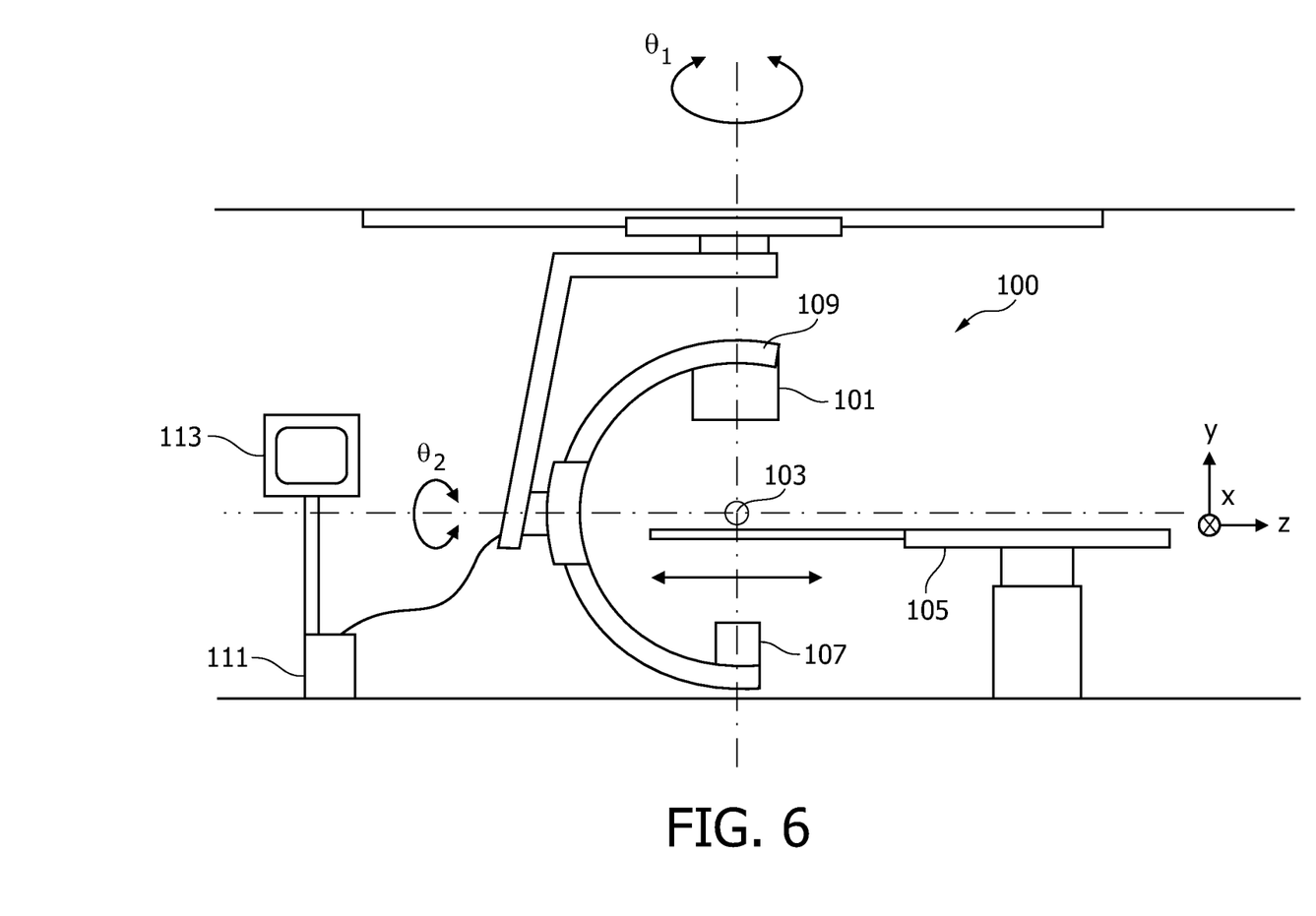
FIG. 6 shows an ablation treatment planning device comprising a conventional C-arm X-ray imaging device.

In FIG. 2, a volume rendered image is shown. Such image may be based on a 3D image data set acquired with an X-ray imaging device from a region of interest. For example, an ablation treatment planning system 100 may comprise such X-ray imaging device such as e.g. a C-arm system as shown in FIG. 6 which is adapted to acquire a plurality of X-ray projection images under various image acquisition angles such that, finally, a 3D image data set may be generated from the plurality of 2D projection images. Therein, an X-ray source 101 attached to a first end of a C-arm 109 may emit X-rays which are transmitted through a region of interest 103 within a patient (not shown) lying on a displaceable table 105. The X-rays are then detected with an X-ray detector 107 attached to a second end of the C-arm 109. Therein, the C-arm may be moved and rotated to various positions and orientation and various 2D projection images may be acquired and transmitted to a controller 111 comprising a computer and a memory. The various 2D projection images may be used to generate a 3D image data set. Such 3D image data set may represent a volume rendered image of the region of interest such as the image including a spine, some ribs and a kidney of a patient as shown in FIG. 2.

In such 3D image data set, 3D model data of an ablation volume 1 are introduced. As will be explained in further detail below, the introduction of the 3D model data of the ablation volume into the 3D image data of the region of interest may be performed in a specific way using a stencil buffer such that 3D image data representing pixels may be "tagged" in a specific way such that, in a subsequent processing step, such tagged pixels may be blended into a color buffer before finally drawing the 2D image to be visualized.

Figure 2A:
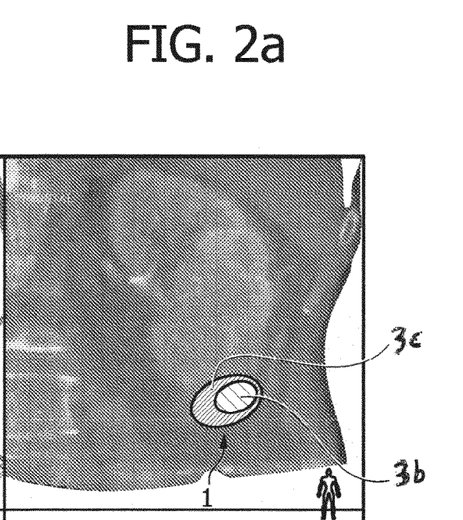
Figure 2B:
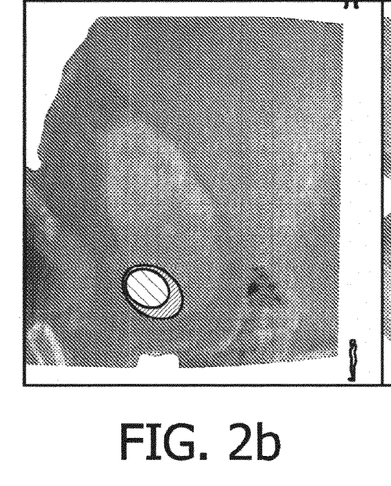
Figure 2C:
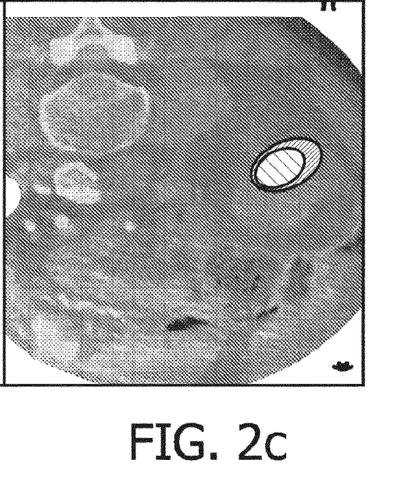

FIGS. 2a, 2b, 2c show clipped cross-sectional ablation areas of the ablation volume 1 positioned in the kidney of the patient in a frontal view (FIG. 2a), lateral view (FIG. 2b) and an axial view (FIG. 2c). Herein, "clipping" may mean that a clipping plane is used to clip, i.e. "hide", a region of the represented three-dimensional space. Accordingly, a clipping plane may be a plane that separates the represented space into two regions, one region is included from the viewing volume, the other is excluded from the viewing volume. For example, if a half sphere would have to be drawn, a clipping plane may be used that "slices" a sphere and only draws half of it.

The visual representations shown in FIGS. 2, 2a, 2b, 2c may not be optimum for practical use for a physician. Only the inside of the spheroid ablation volume 1 may be relevant whereas the outside thereof may be distracting and may even be present if the intersecting MPR plane is behind the ablation volume. Furthermore, the shaded rendering may fully hide important clinical information comprised in the 3D image data set.

In order to improve the visualization, a 3-steps drawing sequence that uses a stencil buffer as for instance provided by OpenGL® or DirectX® is proposed:

1. In a first step, by culling its outside, only the inside of the spheroid ablation volume will be drawn/tagged through the MPR clip-plane in the stencil buffer;

2. In a second step, by culling the inside, the outside of the spheroid ablation volume will be rendered to the stencil buffer through the MPR clip-plane and those pixels that are part of the outside and that were tagged in the first step are reset;

3. Now, in a third step, the tagged pixels are blended to the color buffer.

Herein, a "stencil buffer" may be similar to the color buffer with the exception that pixels in the stencil buffer do not represent colors but may have an application-specific meaning. The stencil buffer may not be directly visible in the finally drawn image like the color buffer, but bits in the stencil planes may form an unsigned integer tag that effects and may be updated by drawing commands, through stencil function and stencil operations. The stencil function may control whether a fragment is discarded or not by a stencil test, and the stencil operation may determine how the stencil planes are updated as a result of that test. The stencil test may be operated on 2D pixels during a final step of rasterization when drawing the 2D image. The test may be controlled by means of the StencilFunc. The stencil operation is a comparison between the value in the stencil buffer for a destination pixel and a stencil reference value (specified for this operation). If stencilling is enabled, an application can control, using glStencilOp, what happens under three different scenarios: (1.) The stencil test fails; (2.) The stencil test passes but the depth test fails; and (3.) Both, the stencil test and the depth test pass.

The term "culling" refers to an operation used to reduce fill-limited drawings by backface or frontface removal. If a polygon normal is facing away from a viewer then it is "backfacing". Backface culling is a process by which polygons (usually triangles) that are not facing a camera are removed from a rendering pipeline. For example, if one is drawing a sphere, half of its polygons are backfacing at any given time. Backface culling is enabled by default. Drawing backfaced polygons may be useful when two side shading is enabled to look from the inside or to draw the inside of partially open or clipped objects. If frontface culling is enabled, only the back/inside of an object is rendered.

In the following, the above indicated 3-steps drawing sequence for ablation volume tagging will be described in more detail and a suitable computer program code comprising OpenGL® commands is provided for clarifying to someone skilled in the art a computational implementation of the proposed ablation treatment planning method according to an embodiment of the present invention.

At a point an ablation rending is operated, modeling and viewing transformations are setup and the cross sectional volumes slices are interpolated and displayed. At this point the modeling and viewing transformation will be setup to configure the planned ablation orientation, position and scaling of the sphere.

The cross sectional elliptical projection is obtained by a three step process.

glStencilOp(GL_KEEP, GL_KEEP , GL_REPLACE);
    glStencilFunc(GL_ALWAYS, STENCILMASK_EL-IPSE_INSIDE, 0);
    glColorMask(GL_FALSE, GL_FALSE, GL_FALSE, GL_FALSE);
    glEnable(GL_CULL_FACE);
    glCullFace(GL_FRONT);
    gluSphere(term_length);

In this first step only the inside of the projected sphere will be drawn, by culling the front-faces. By the colorMask operation this will not affect the color buffer but only the stencil buffer. The stencil buffer is setup such that the pixels that will be drawn are labeled STENCILMASK_ELIPSE_INSIDE. Note that, as shown above, by drawing the inside, if the clipplane is in front of the center of the ablation, to much of the projected cross section is drawn. This will be corrected in the next step.

glCullFace(GL_BACK);
    glStencilOp(GL_KEEP, GL_KEEP, GL_ZERO);
    glStencilFunc(GL_EQUAL, STENCILMASK_EL-IPSE_INSIDE, SLICEMASK_ALL);
    gluSphere(therm_length);

In this second step only the front faced triangles that make up the sphere will be drawn by culling the backfaces. The stencil operation is set such that only INSIDE labeled stencil pixels will be touched and the affected pixels will be set to 0. Note that at this point, the correct cross section, labeled STENCILMASK_ELIPSE_INSIDE is now rendered in the stencil buffer.

glStencilOp(GL_KEEP, GL_KEEP, KEEP);
    glStencilFunc(GL_EQUAL, STENCILMASK_EL-IPSE_INSIDE);
    glColor4fv(ablationColor);
    glColorMask(GL_TRUE, GL_TRUE, GL_TRUE, GL_TRUE);
    glCullFace(GL_FRONT);
    gluSphere(term_length);

Finally in the third step the color buffer is made active again (glColorMask).The outside faces are rendered to the color buffer for those pixels that are labeled STENCILMASK_E-LIPSE_INSIDE by the previous operation. The pixels are rendered transparently (alpha blending) on top of the volume information.

After the image rendering and prior to an ablation drawing, a correct model transformation that scales, positions and transforms the ablation area in a direction of an ablation needle is set up. The ellipsoids are drawn as spheres in a scaled coordinate system. Furthermore, the stencil buffer and clip plane will need to be initialized.

Figure 3A:
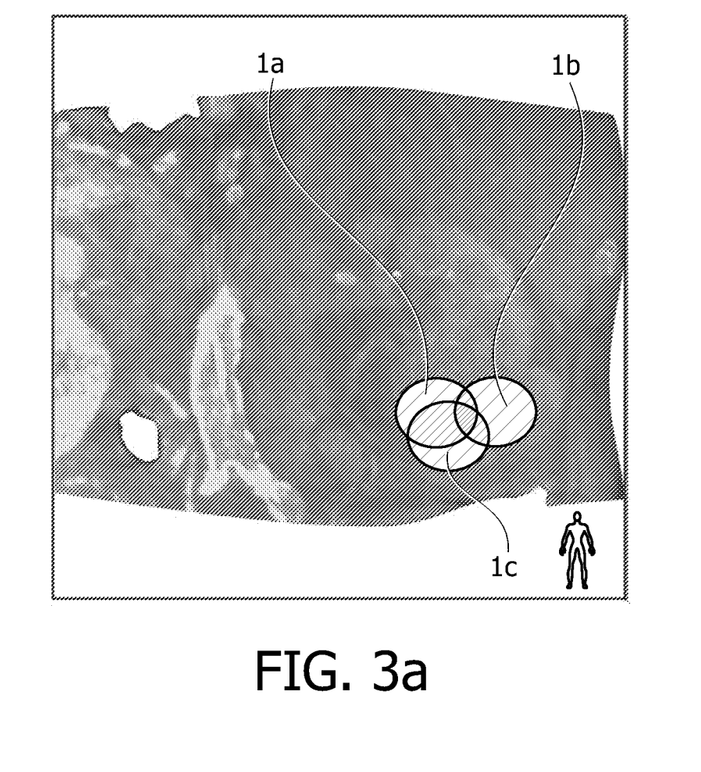
FIG. 3a,b show a representation of a plurality of spheroid ablation volumes wherein overlapping ablation areas are visualized in a superimposed way.

An example of a result of the above 3-step drawing sequence is shown in FIG. 3a. Therein, three overlapping ablation volumes 1a, 1b, 1c have been introduced into a 3D image. Overlapping ablation areas are drawn by the rendering scheme as described above.

Figure 3B:
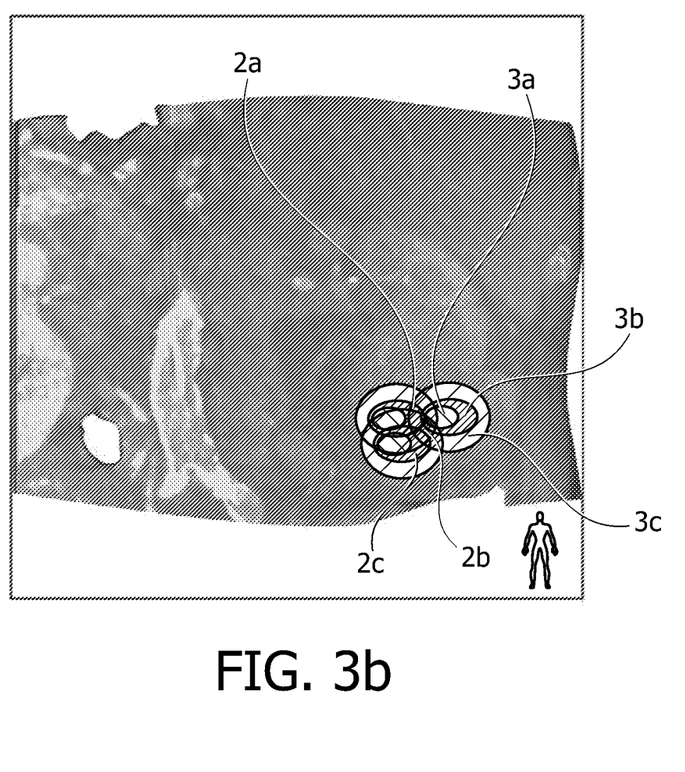

In FIG. 3b, multiple isotherms represented as ablation regions 3a, 3b, 3c as they may be defined for the various cryoablation needles are visualized in three different colors (indicated in FIG. 3b as different patterns).

As shown in the images of FIG. 3a,b, the partially overlapping ablation areas 1a, 1b, 1c are visualized superimposed on-top of each other which produces ablation area representations 2a, 2b, 2c having different transparency levels. Such different transparency levels may complicate an image interpretation to be made by a physician.

Figure 4A:
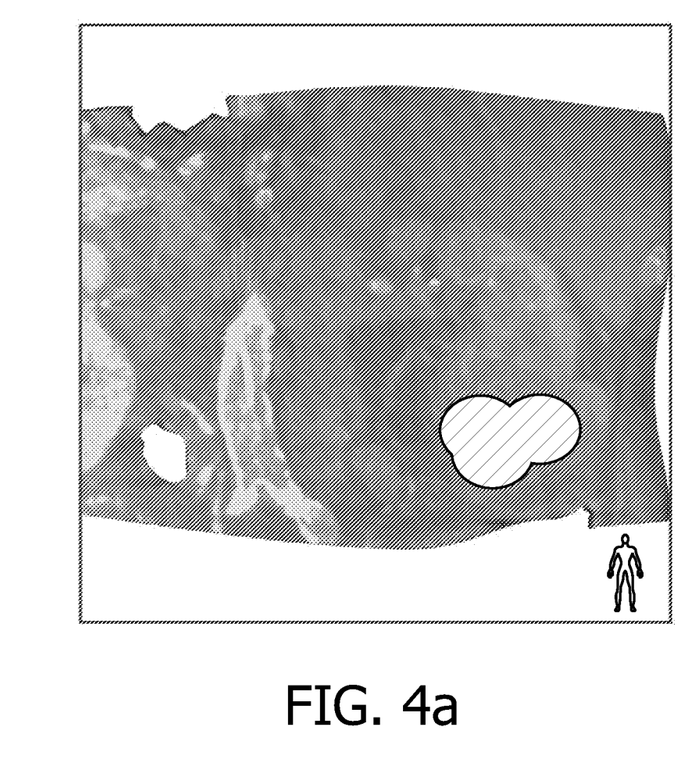
FIG. 4a,b show a representation of a plurality of spheroid ablation volumes wherein overlapping ablation areas are visualized in a non-superimposed way.
Figure 4B:
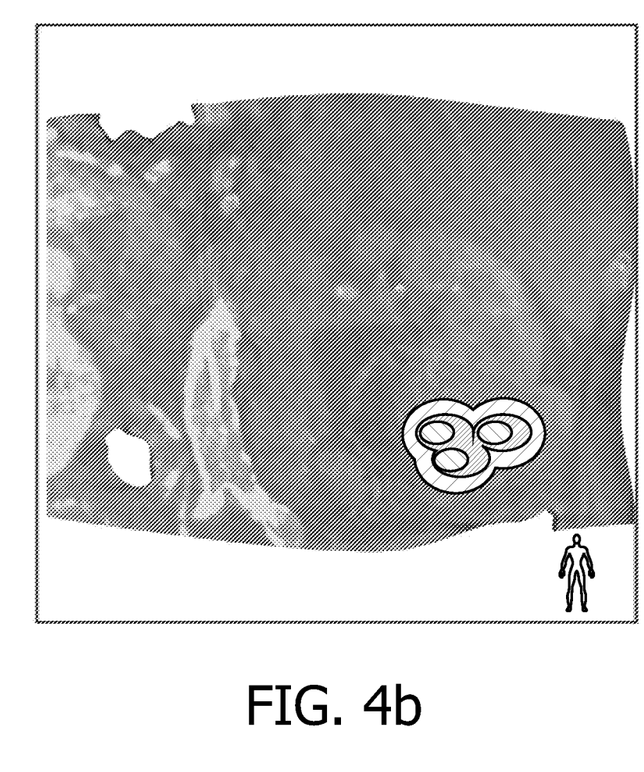

Therefore, as shown in FIGS. 4a, 4b, a representation with a drawn 2D image in which a plurality of tagged portions corresponding to a plurality of ablation volumes are blended into the color buffer such that profiles representing the ablation volumes do not overlap, may be a preferred visualization. Such non-overlapping presentation may provide for an easier image interpretation, particularly in the case of multiple isotherms as shown in FIG. 4b.

In order to avoid the overlapped presentation some modifications to the above rendering scheme have to be made.

1. glStencilOp(GL_KEEP, GL_KEEP, GL_REPLACE);
    glStencilFunc(GL_NOTEQUAL, STENCILMASK_EL-IPSE_INSIDE, STENCILMASK_ELIPSE_INSIDE);
    glColorMask(GL_FALSE, GL_FALSE, GL_FALSE, GL_FALSE);
    glEnable(GL_CULL_FACE);
    glCullFace(GL_FRONT);
    gluSphere(term_length);

2. glStencilOp(GL_KEEP, GL_KEEP, GL_ZERO);
    glStencilFunc(GL_EQUAL, STENCILMASK_EL-IPSE_INSIDE, STENCILMASK_ELIPSE_INSIDE);
    glCullFace(GL_BACK);
    gluSphere(term_length);

3. glStencilOp(GL_KEEP, GL_KEEP, KEEP);
    glStencilFunc(GL_EQUAL, STENCILMASK_EL-IPSE_INSIDE, STENCILMASK_ELIPSE_INSIDE);
    glColor4fv(ablationColor);
    glColorMask(GL_TRUE, GL_TRUE, GL_TRUE, GL_TRUE);
    glCullFace(GL_FRONT);
    gluSphere(term_length);

The stencil buffer is now setup such that only stencil values not-equal to STENCILMASK_ELIPSE_INSIDE will be drawn and labeled STENCILMASK_ELIPSE_INSIDE in subsequent ablation cross-section presentations.

Furthermore in order to take care that in the case of multiple cryo-ablation isotherm presentation the inner (more colder) ablation area's overlap the outer (lesscold) areas, the ablation profile need to be drawn in a specific order. The profiles need to be drawn from inside out, so first all colder profiles then all less cold etc. This can be described as:

for all ablations:
    draw −40 degree isotherm
    draw −20 degree isotherm
    draw 0 degree isotherm Needle Planning It will be clear that the planning and guiding of the needles and the planning of ablation areas are closely related.

There are various ways of defining a needle target point and entry point/direction. One way is e.g. presented in WO 2008/139 354 A2.

An orientation of the ablation volume in relation to a needle target location is usually defined by the device manufactures. In case of cryoablation (see FIG. 1), this relation is defined by the so-called Ice Front (in front of the needle tip).

The ablation volume can be drawn relative to the needle target location by a procedure as shown below.

void DrawAblationIsoTerm(Vector3D& needleTarget, Matrix16D& neeldleRotation, IsoTherm therm)

```
{
    double therm_length= therm.m_length/2, therm_width=
therm.m_width/2, therm_front= therm.m_front;
    Vector3D dir= needleRotation* Vector3D(0,0,1);
    Vector3D ablatonTarget= needleTarget+ (dir* (therm_length-
    therm_front));
    glPushMatrix( );
        glLoadIdentity( );
        glTranslated(ablatonTarget.x ablatonTarget.y ablatonTarget.z);
        glMultMatrixd(needleRotation );
        glScaled(therm_width/ therm_length,
        therm_width/therm_length, 1.0);
        if (!m_ablation_ellipse) m_ablation_ellipse =
        gluNewQuadric( );
        gluQuadricDrawStyle (m_ablation_ellipse, GLU_FLAT);
        //First draw Clipped Inside
        glDisable(GL_DEPTH_TEST);
        glColor4fv(m_ablationColor);
        glStencilFunc(GL_NOTEQUAL,
STENCILMASK_ELIPSE_INSIDE,
STENCILMASK_ELIPSE_INSIDE);
        glStencilOp(GL_KEEP, GL_KEEP , GL_REPLACE);
        glColorMask(GL_FALSE, GL_FALSE, GL_FALSE,
        GL_FALSE);
        glEnable(       GL_CULL_FACE );
        glCullFace( GL_FRONT);
        gluSphere(m_ablation_ellipse, therm_length, 100, 100);
        //Draw The clipped outSide
        glCullFace( GL_BACK);
        glStencilOp(GL_KEEP, GL_KEEP , GL_ZERO);
        glStencilFunc( GL_EQUAL,
STENCILMASK_ELIPSE_INSIDE, SLICEMASK_ALL);
        gluSphere(m_ablation_ellipse, therm_length, 100, 100);
        //Draw through inside stencil
        glStencilOp(GL_KEEP, GL_KEEP, GL_INCR);
        glColorMask(GL_TRUE, GL_TRUE, GL_TRUE,
        GL_TRUE);
        glStencilFunc( GL_EQUAL,
STENCILMASK_ELIPSE_INSIDE, SLICEMASK_ALL);
        glCullFace( GL_FRONT);
        gluSphere(m_ablation_ellipse, therm_length, 100, 100);
    glPopMatrix( );
    glDisable(      GL_CULL_FACE );
}
```

Figure 5A:
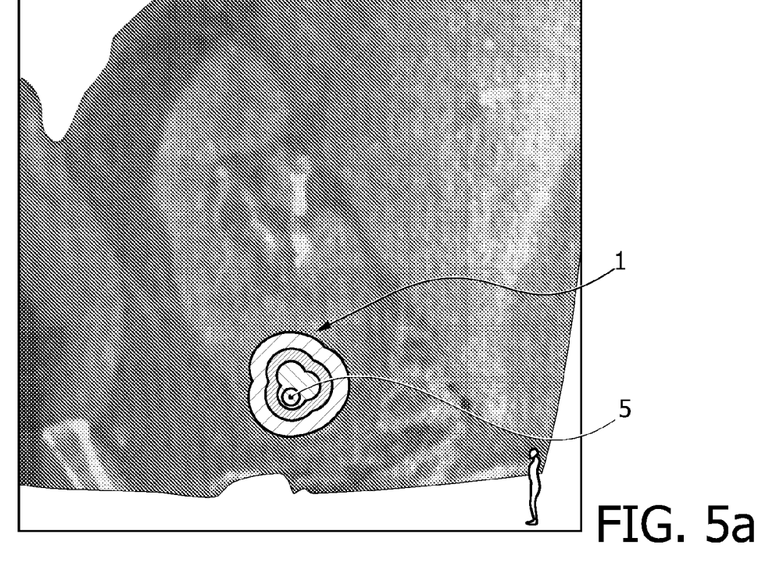
FIGS. 5a-e show a planned overall ablation volume composed from three spheroid ablation volumes in an entry point view (FIG. 5a) as well as in multiple orthogonal views (FIG. 5c,d,e).
Figure 5B:
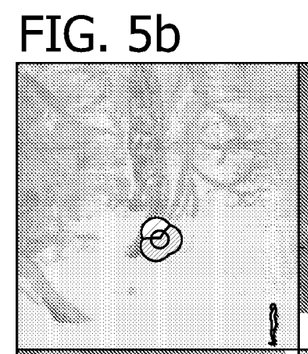
Figure 5C:
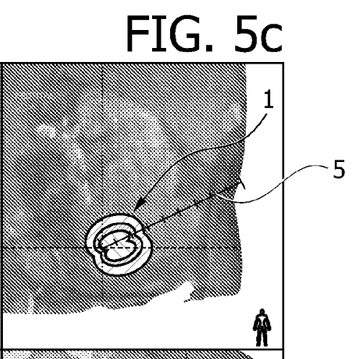
Figure 5D:
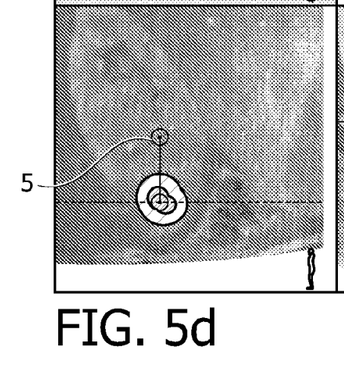
Figure 5E:
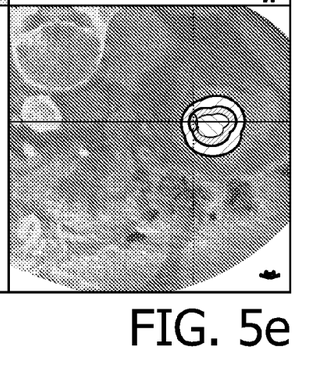

The image in FIG. 5a shows three ablations, planned parallel next to each other, in the entry point view, i.e. the plane that is orthogonal to the needle directions. FIGS. 5b, 5c, 5d, 5e show multiple orthogonal views on the same ablations. Note that the current needle 1 is shown in these presentations.

For an actual intervention, a C-arm X-ray imaging system may first be arranged such as to acquire images in the entry point view. In such view, the needle is projected as a single point in the correct direction and without parallax as long as the C-Arm X-ray source is correctly oriented on the extension of the planned needle trajectory The needle may then be inserted to a certain degree so as to be guided in its orientation. Then, the C-arm system may be rotated about 90° such as to acquire images in a plane including a longitudinal direction of the needle. In such orientation, a further insertion of the needle may be monitored and it may be observed whether the needle has finally attained its planned location.

Multiple Needle Ablation Planning

For the insertion of multiple needles it is advantageous to position the needles parallel to a first or a selected needle. In this way the ablation profiles/needles can be positioned in parallel relative to each other. Here based on the ablation profile's position and orientation, the needle target (ice front) and entry point (cross section with skin) may be calculated.

For the insertion of temperature sensors, additional needles without ablation profiles can be planned and positioned relative to the isotherms.

In another configuration, the ablation can be planned prior to the intervention on pre-interventional multi-modality data (MR/CT/XperCT) image data, and transformed to the interventional situation by means of 3D/3D registration, with a (fast scan) interventional acquisition.

Summarizing, an ablation treatment planning and, optionally, guiding method usable for e.g. tumour tissue ablation with a cryoablation needle which cools down an adjacent tumour tissue to thereby generate an ablation volume is proposed. In order to be able to plan an ablation treatment, a 3D image data set of a region of interest may be acquired by e.g. X-ray imaging using e.g. a C-arm system. Then, 3D model data of the ablation volume are introduced into the 3D image data set for example by tagging image pixels using a stencil buffer and possibly by culling specific inside areas and/or outside areas of the ablation volume. Finally, a 2D image to be visualized to a physician and comprising a projection of the region of interest and the ablation volume is drawn wherein an MPR (multi planar reformatting) plane in which the 2D image is drawn is used as a clipping plane. With such graphical approach, an ablation volume having any arbitrary shape such as for example an ellipsoid shape may be visualized within a 3D image space by drawing 2D images in any desired MPR plane such that also oblique orientations of the ablation volume can be represented. In a subsequent guiding procedure, an ablation needle may be guided to a location and in an orientation as previously planned.

It should be noted that the term "comprising" does not exclude other elements or steps and that the indefinite article "a" or "an" does not exclude the plural. Also elements described in association with different embodiments may be combined. It should also be noted that reference signs in the claims shall not be construed as limiting the scope of the claims.

The invention claimed is:

1. An ablation treatment planning device configured for acquiring a three-dimensional (3D) image data set of a region of interest, said device comprising a graphic processing computer configured for introducing 3D model data of an ablation volume into the 3D image data set and for drawing, as a 2D image, what remains of a cross sectional multiplanar reformatting (MPR) slice of said region of interest and said ablation volume within said MPR plane by virtue of using said MPR plane as a clipping plane, said device further comprising an X-ray imaging device for said acquiring.

2. The device of claim 1, said computer being further configured to cut away image content of said ablation volume so as to leave, for said drawing, the remainder of said slice.

3. The device of claim 2, said computer being further configured for preparing to perform said drawing, by substituting, for the cut away image content, other image content which is thereby part of the drawn 2D image.

4. The device of claim 3, said other image content comprising a graphical symbol.

5. The device of claim 2, further comprising a buffer for receiving said 2D image to be drawn.

6. The device of claim 5, said computer being operable for, in said drawing, tagging portions of said 3D model data through the MPR plane in a stencil buffer, and configured for blending the tagged portions to said buffer, serving as a color buffer for subsequent drawing of the 2D image.

7. The device of claim 6, operable, in a first step, to cull an outside of the ablation volume such that only an inside of the ablation volume is tagged through the MPR plane in the stencil buffer and, in a second step, to cull an inside of the ablation volume such that the outside of the ablation volume is rendered through the MPR plane in the stencil buffer wherein those pixels being part of the outside of the ablation volume and being tagged in the first step are reset before blending to the color buffer.

8. The device of claim 6, operable to introduce, into the 3D image data set, 3D model data of a plurality of ablation volumes and configured to blend, into the color buffer, a plurality of the tagged portions corresponding to the plurality of ablation volumes such that profiles representing the ablation volumes do not overlap.

9. An ablation treatment planning and guiding device comprising the device of claim 5 and a display, said computer being further configured for reading data from said buffer and for visualizing, via said display, data from said buffer as graphics drawn by said drawing.

10. The device of claim 1, said using resulting in a gapless planar region being, for said drawing, omitted from said slice.

11. The device of claim 1, said computer being further configured for introducing, into said 3D image data set, 3D model data of another ablation volume that intersects said slice and for drawing, as another 2D image, what remains of said slice by virtue of using said MPR plane as a clipping plane with respect to both volumes.

12. The device of claim 11, further configured for cutting away image content of both volumes, one of said volumes overlapping in said slice with the other of said volumes, said using leaving the remainder of said slice with an outer outline of said both volumes.

13. The device of claim 12, said drawing omitting depiction of outlines, of said volumes, that are within the overlap.

14. A non-transitory computer readable medium for ablation treatment planning, said medium embodying a computer program having instructions executable by a processor for performing a plurality of acts, among said plurality there being the acts of:
(a) acquiring a three-dimensional (3D) image data set of a region of interest; (b) introducing 3D model data of an ablation volume into the 3D image data set; and (c) drawing, as a 2D image, what remains of a cross sectional multiplanar reformatting (MPR) slice of the region of interest and the ablation volume within said MPR plane by virtue of using said MPR plane as a clipping plane.

15. An ablation treatment planning method, comprising: (a) acquiring a three-dimensional (3D) image data set of a region of interest; (b) introducing 3D model data of an ablation volume into the 3D image data set; and (c) drawing, as a 2D image, what remains of a cross sectional multiplanar reformatting (MPR) slice of the region of interest and the ablation volume within an MPR plane by virtue of using the MPR plane as a clipping plane.

16. The ablation treatment planning method of claim 15, further comprising setting up, prior to step (c), a model transformation for at least one of scaling, positioning and transforming the 3D model data of the ablation volume in a predetermined direction.

17. The ablation treatment planning method of claim 15, wherein the 3D model data represent a spheroid ablation volume having a main symmetry axis corresponding to a center axis of an ablation needle.

18. The ablation treatment planning method of claim 15, wherein at least one of an ablation volume location, an ablation volume orientation and a number of ablation volumes is determined according to a user input.

19. An ablation treatment planning and guiding method, comprising planning an ablation volume within a region of interest using at least one 2D image drawn in accordance with the method according to claim 15, wherein a location and orientation of the ablation volume is predetermined by a location and orientation of at least one ablation needle, said method further comprising guiding an ablation needle into the region of interest in accordance with a planned orientation and location.

20. The ablation treatment planning and guiding method of claim 19, wherein the guiding of the ablation needle is monitored using an X-ray imaging device.

21. The ablation treatment planning and guiding method of claim 20, further comprising: monitoring an entry point of the ablation needle while the X-ray imaging device is oriented along the planned orientation; and monitoring a final inserted location of the ablation needle while the X-ray imaging device is oriented perpendicular to the planned orientation.

* * * * *